United States Patent [19]

Mathies et al.

[11] Patent Number: 4,902,277
[45] Date of Patent: Feb. 20, 1990

[54] CIRCULATING A LIQUID THROUGH A JOINT

[75] Inventors: Burkhard Mathies, Givrins; Didier Misse, Grand-Saconnex; Claude Guignard, St. Genis-Pouilly; Paul Pidoux, Bassins, all of Switzerland

[73] Assignee: Orthoconcept, Meyrin, Switzerland

[21] Appl. No.: 89,740

[22] Filed: Aug. 26, 1987

[51] Int. Cl.$^4$ .............................................. A61M 1/03
[52] U.S. Cl. ..................................... 604/67; 604/118; 604/154
[58] Field of Search ............... 604/118, 119, 120, 121, 604/151, 152, 153, 65, 66, 67, 22, 27, 28, 30, 31, 32, 19, 35, 49, 50, 51; 917/2, 38

[56] References Cited

U.S. PATENT DOCUMENTS

| | | | |
|---|---|---|---|
| 3,900,022 | 8/1975 | Widran | 604/118 |
| 4,007,742 | 2/1977 | Banko | 604/118 |
| 4,203,444 | 5/1980 | Bonnell et al. | 604/22 |
| 4,261,360 | 4/1981 | Perez | 604/67 |
| 4,423,727 | 1/1984 | Widran et al. | 128/748 |
| 4,493,694 | 1/1985 | Wuchinich | 604/22 |
| 4,604,089 | 8/1986 | Santangelo et al. | 604/5 |
| 4,650,462 | 3/1987 | DeSatnick et al. | 604/30 |
| 4,662,871 | 5/1987 | Rufelson | 604/119 |
| 4,671,792 | 6/1987 | Borsanyi | 604/153 |
| 4,750,902 | 6/1988 | Wuchinich et al. | 604/22 |
| 4,795,424 | 1/1989 | Burner | 604/30 |

FOREIGN PATENT DOCUMENTS

| | | | |
|---|---|---|---|
| 86/00534 | 1/1986 | World Int. Prop. O. | 604/151 |
| 86/01390 | 3/1986 | World Int. Prop. O. | 604/30 |

OTHER PUBLICATIONS

Morgan; "Fluid Delivery Systems for Arthroscopy", Arthroscopy, 1987, 3(4) pp. 288-291.
Bergstrom et al.; "The Use of an Infusion Pump in Arthroscopy", Arthroscopy, 1986, 2(1) pp. 41-45.

*Primary Examiner*—C. Fred Rosenbaum
*Attorney, Agent, or Firm*—Herbert Dubno; Andrew Wilford

[57] ABSTRACT

For an endoscopic resection or examination of a body cavity or joint where a physiological liquid is pumped at one location to a joint from a feed conduit connected to a feed pump and withdrawn at another location from the joint through a suction conduit connected to a suction pump, this suction pump is operated at a rate corresponding to a generally constant low rate of flow in the suction conduit and the feed pump is operated in accordance with the pressure detected in the joint to maintain the pressure above a predetermined desired level. Furthermore when a tool carrying one end of an auxiliary suction conduit is inserted into the joint so that periodically this conduit can be connected to the pump so that liquid can be withdrawn from the joint through this auxiliary conduit, the method comprises the step of automatically increasing the suction-pump rate when the auxiliary conduit is connected to the suction pump to a predetermined relatively high rate. When the tool includes a blade and a motor operable to move the blade, the method further comprises the step of automatically disconnecting the suction pump from the main suction conduit and to the auxiliary suction conduit and simultaneously increasing the suction-pump rate from the low rate to the high rate when the motor is operated to move the blade.

11 Claims, 1 Drawing Sheet

CIRCULATING A LIQUID THROUGH A JOINT

FIELD OF THE INVENTION

The present invention relates to a method of and apparatus for circulating a physiological liquid through a joint while controlling the pressure and flow rate of the liquid. More particularly this invention concerns the control of pressure and flow rate of liquid in an endoscopic resection and/or examination tool.

BACKGROUND OF THE INVENTION

In the endoscopic examination or surgery of a joint and in many other styles of examination, surgery, and treatment it is necessary to pump a physiological liquid, typically a sterile saline solution, into one location of the joint or other area being worked on and to evacuate it at an adjacent location. This is particularly the case in the arthroscopic examination of the knee in which an image of the joint is transmitted to a video display by a fiber-optic cable carried on the tool inserted into the knee joint. This technique is used also to inspect the meniscus, knee ligaments, the sinoviale of cartilage, and the socket of the femur and tibia as well as to operate on certain conditions such as a ruptured miniscus, a folded synovial, a bone chip, or just to rinse out the knee joint.

With such a surgical tool it is necessary not only to control the pressure (force/unit of area) of the liquid being injected into the joint, but also to be able to control its flow rate (volume/unit of time). During a simple examination where no blood or excised particles are freed flow rate is not critical but when doing an endoscopic resection with the concomitant generation of unwanted particles it is necessary to be able to increase the flow rate and thus maintain visibility while ridding the joint of unnecessary material. This is normally done by using a special-duty auxiliary conduit which can be moved by the doctor to a location where material is to be aspirated.

Thus the liquid-feed apparatus normally comprises a main suction conduit that is implanted without possibility of substantial movement other than removal at the top of the joint, a feed conduit that is connected to the pump output and that is implanted in the knee opposite the main suction conduit, and an auxiliary suction conduit that passes through the tool and opens adjacent its reversible rotary blade. Thus material cut off and ground up by the endoscopic tool can be aspirated right at the site it is cut from.

As a result in order to control this device it is necessary to provide a switch for reversing the motor driving the blade, a switch that can turn on or off the motor, one that can raise and lower the suction and/or feed pump rate, and one that can select between which one of the suction conduits is connected to the pump intake. This makes it possible to switch on the tool-mounted suction line when using the tool, and also allows the device to be used without operation of the tool, simply for examination and/or aspiration purposes. Typically these functions are controlled by foot pedals to leave the hands of the surgeon free.

In general the tools of this type in current use are both excessively complex to operate and difficult to control accurately.

OBJECTS OF THE INVENTION

It is an object of the present invention to provide an improved method of and apparatus for controlling liquid flow in an endoscopic resection tool or the like.

Another object is the provision of such a method and apparatus which provide a high degree of control to the doctor operating the machine while remaining extremely simple to use.

SUMMARY OF THE INVENTION

An apparatus for circulating a physiological liquid at a pressure and flow rate through a body cavity for an endoscopic resection or examination of the cavity has a source of the liquid, an input pump connected to the source and having a main feed conduit extending into the cavity for suppling the liquid to same, and an input controller having a sensor for detecting pressure in the joint and for stopping the input pump when the detected pressure varies beyond a predetermined range. A suction pump has a suction conduit extending into the cavity for aspirating the liquid therefrom and is operated by a controller that detects the throughput of the suction pump and stops it when the detected throughput varies beyond another predetermined range.

The suction pump is a volumetric pump having a drive motor and the suction controller includes a tachometer connected to the motor, means for generating a motor-speed set point, and a comparator having inputs connected to the last-mentioned means and to the tachometer for comparing the actual motor speed detected with the motor-speed set point and having an output operatively connected to the motor for slowing same when the actual speed exceeds the set point and for speeding up the motor when the actual speed drops below the set point.

In accordance with a further feature of this invention the set-point generating means can generate two different set points and can alternately selectively feed same to the comparator. In addition the device has a suction-pump shutdown switch connected between the suction pump and the comparator, means for generating a low-pressure limit output, and another comparator connected to the low-pressure output generator means and to the sensor for opening the shutdown switch and stopping the suction pump when the pressure detected by the comparator is less than the low-pressure limit.

Furthermore the device of this invention has a tool insertable into the joint, a second suction conduit having an end opening at the tool and an opposite end, and a valve having an output connected to the suction pump and two alternately selectable inputs, one connected to the first-mentioned suction conduit and the other to the second suction conduit. The valve can move between a position connecting the suction pump to only the first suction conduit and a position connecting the suction pump to only the second suction conduit. The tool of the apparatus also has a blade and the apparatus further comprises a switch closable for rotating the blade.

Thus according to this invention the suction pump is operated at a rate corresponding to a generally constant low rate of flow in the suction conduit and the feed pump is operated in accordance with the detected pressure in the joint to maintain the pressure above a predetermined desired level.

Furthermore when a tool carrying one end of an auxiliary suction conduit is inserted into the joint so that periodically this conduit can be connected to the pump so that liquid can be withdrawn from the joint through this auxiliary conduit, the method comprises the step of automatically increasing the suction-pump rate when the auxiliary conduit is connected to the suction pump to a predetermined relatively high rate. When the tool includes a blade and a motor operable to move the blade, the method further comprises the step of automatically disconnecting the suction pump from the main suction conduit and to the auxiliary suction conduit and simultaneously increasing the suction-pump rate from the low rate to the high rate when the motor is operated to move the blade.

DESCRIPTION OF THE DRAWING

The above and other objects, features, and advantages will become more apparent from the following, reference being made to the accompanying drawing in which.

SPECIFIC DESCRIPTION

Figure 1:
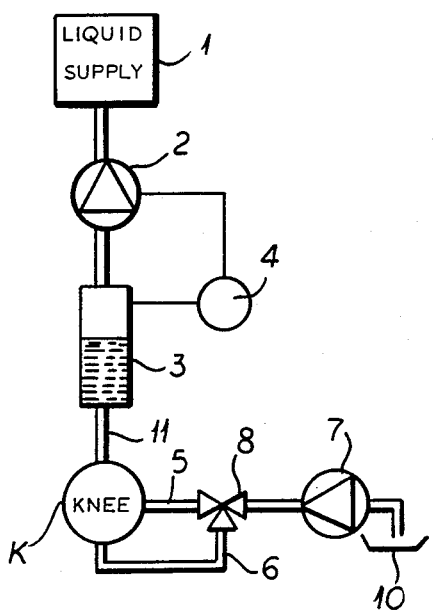
FIG. 1 is a block diagram illustrating the basics of an endoscopic procedure.

As seen in FIG. 1 a standard endoscope resection of a knee shown at circle K entails injecting a liquid from a source 1 into one side of the joint K and aspirating it from the opposite side of the joint K to a sump 10. A pump 2 pulls the liquid from the source 1 and injects into an accumulator 3 whose pressure is monitored by a sensor 4 to control the speed of this pump 2 and the liquid passes from the accumulator 3 through a feed conduit 11 into the joint K. The liquid is withdrawn via a conduit 5 implanted in the joint K in one place for the resection or examination or via another conduit 6 actually carried on the resection tool shown at 9 in FIG. 2 and movable therewith in the joint K. A three-way valve 8 is connected between these conduits 5 and 6 and a suction pump 7 that empties into the sump 10. Thus this pump 7 can suck from either of the conduits 5 and 6 depending on the position of the valve 8.

Figure 2:
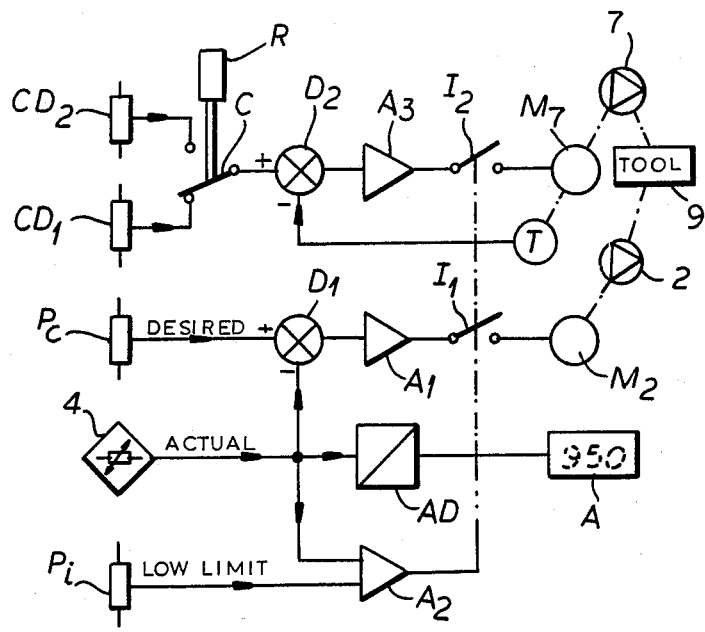
FIG. 2 is a schematic diagram of the rate and pressure controls of the instant invention.

As further illustrated in FIG. 2, according to this invention the throughput or flow rate of the pump 2 is varied to keep the pressure in the joint at a certain level. This is achieved by powering the pump 2 from a variable-speed electric motor $M_2$ in turn controlled by an amplifier $A_1$ whose output in turn is a function of the output of a comparator $D_1$. This element $D_1$ compares the actual-value output of the pressure sensor 4, which output is directly related to the pressure in the joint K, and a set point or desired-value signal from a generator $P_c$. The actual-value output of the sensor 4 is also fed through an analog/digital converter AD to a display A and to one input of another comparator $A_2$ receiving a lower-limit set point from a generator $P_i$ and connected to a switch $I_1$ in series between the amplifier $A_1$ and the motor $M_2$. Thus before surgery the doctor sets the generator $P_i$ for the lowest permissible pressure in the joint K and the generator $P_c$ for the normally somewhat higher desired pressure in the joint K. During the operation the system will read out the actual pressure on the display A while maintaining the joint pressure at the desired value of the generator $P_c$ by appropriately speeding up or slowing down the pump 2. When the pressure drops below the rarely changed lower limit of the generator $P_i$, something that happens for instance when the supply 1 runs out, the pump 2 is shut down by the switch $I_1$.

The throughput or flow rate of the pump 7 is varied to one of two preset levels selected alternately as described below according to demand. To this end the pump 7 is driven by a variable-speed electric motor $M_7$ which is powered through a switch $I_2$ of the comparator $A_2$ from an amplifier $A_3$ itself powered from a comparator $D_2$. One input of this comparator $D_2$ is connected to a tachometer T directly driven from the motor $M_7$ so as to produce an output directly related to motor rotation rate. The other input is connected alternately by an SPDT switch C of a relay R to either of two set-point generators $CD_1$ and $CD_2$. The outputs of these generators $CD_1$ and $CD_2$, which can be simple potentiometers like the generators $P_i$ and $P_c$, are set before surgery by the doctor for high and low evacuation flow rates.

Figure 3:
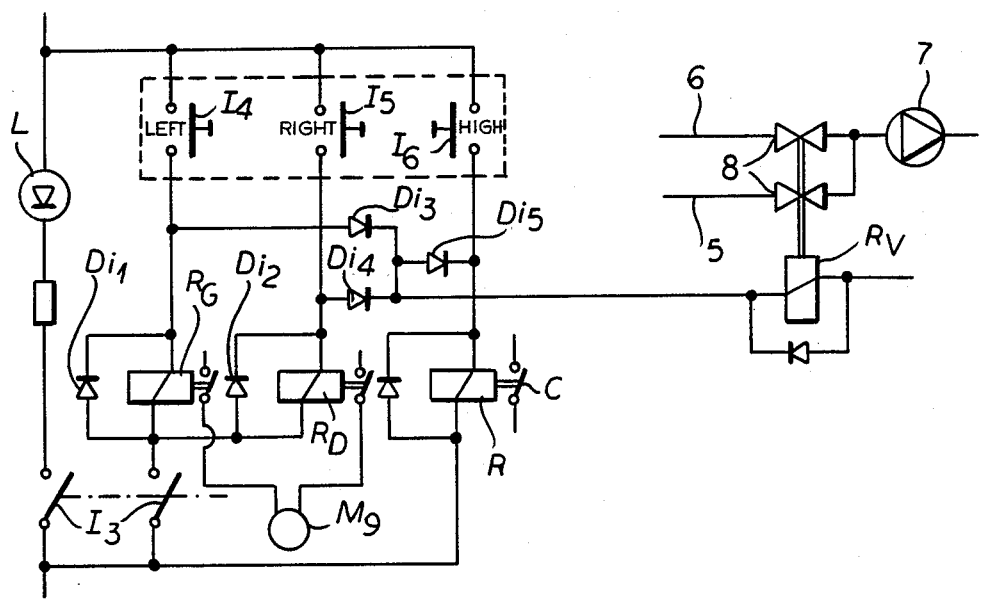
FIG. 3 is a more detailed schematic diagram showing the switching of the various functions of the method and apparatus of the present invention.

FIG. 3 illustrates how the tool 9 has a motor $M_9$ that is reversible for right- or left-hand rotation in accordance with which of two operating relays $R_D$ and $R_G$ is closed. These relays $R_D$ and $R_G$ are connected on the one side to one side of a power source via a main switch $I_3$ that is only closed when the tool 9 is equipped with a blade that is going to be used, this switch $I_3$ also illuminating a pilot light L when closed. On the other sides these relays $R_D$ and $R_G$ are connected via respective normally open switches $I_4$ and $I_5$ to the other side of the electric source. Diodes $Di_1$ and $Di_2$ shunt the relays $R_G$ and $R_D$, respectively. The relay R that operates the switch C for selecting high speed or low speed for the suction pump 7 is energized to close and select the high limit of generator $CD_2$ whenever either of the relays $R_G$ or $R_D$ is energized. This is achieved by connecting this relay R on the one side to one side of the source and on the other side via diodes $Di_3$ and $Di_5$ to the the switch $I_4$ and via a diode $Di_4$ to the switch $I_5$ and through these switches when closed to the other side of the source. A normally open override switch $I_6$ can also be closed to energize the relay R and select the high flow rate even if neither motor switch $I_3$ or $I_4$ of the main on-off switch $I_3$ is closed. Finally a solenoid $R_V$ is connected via the diodes $Di_3$ and $Di_4$ to the motor switches $I_4$ and $I_5$ to switch the pump 7 from the main line 5 to the auxiliary tool line 6 whenever either of the relays $R_G$ or $R_D$ is energized.

Thus in addition to setting the various pressure levels as described below, settings that change little, all the surgeon need do once the device is going is set the switch $I_3$ depending on whether or not any actual cutting was going to be done. During startup it is, of course, essential to override the switch $I_2$ at least until pressure builds up in the joint K.

Thus by using only the three switches $I_4$, $I_5$, and $I_6$, which can be operated easily be a foot pedal with two ranges of movement, the following operations can be done:

When the switch $I_3$ is closed, operating either of the motor switches $I_4$ or $I_5$ will set the motor $M_9$ to rotate the cutter in the tool 9 in the appropriate direction. In addition the relay R will automatically switch the suction pump 7 to high speed and will switch the suction pump 7 to draw from the conduit 6 that opens just at the tool. This is advantageous while cutting to clear excised matter and blood from the site.

When the switch $I_3$ is open, closing either of the motor switches $I_4$ or $I_5$ will have no effect on the motor $M_9$ since the relays $R_G$ and $R_D$ will be open circuited, but as described above will set the suction pump 7 to high speed and will switch over the suction pump input to the tool conduit 6. This is useful for cleaning out a joint with the arthroscope by specifically inserting the tool conduit 6 into the area to be vacuumed after removing the tool from the conduit 6.

Regardless of the position of switch $I_3$, closing only the suction switch $I_6$ will switch the suction pump 7 to a high withdrawal rate, but through the main conduit 7. Since the increased withdrawal rate will reduce the joint pressure, the sensor 4 will detect this and speed up the pump 2 for good flushing of the joint.

When none of the switches $I_4$, $I_5$, or $I_6$ is actuated but the system is pressurized, the relay R is not energized so the comparator $D_2$ is connected to the low-level generator $CD_2$ and the control system of this invention will seek to maintain a low flow through the joint, adjusting suction according to actual conditions while maintaining input fairly constant at a fairly low level.

Thus when an examination tool 9 is used having no blade, the switch $I_3$ is left open and the two possible modes— high suction through the main line 5 or high suction through the tool line 6— are selected by operating either of the switches $I_4$ or $I_5$ and the switch $I_6$, respectively. When the tool has a blade there are three modes— tool rotation to the right with high-rate suction through the tool line 6, tool rotation to the left with high-rate suction through the tool line 6, or high-rate suction through line 5 with no tool rotation— all also selectable by the respective mode switches $I_4$, $I_5$, and $I_6$, respectively. In either case when none of the switches $I_4$, $I_5$, or $I_6$ is actuated the system reverts to a low-pressure operation through the main line 5.

The system of this invention therefore is extremely easy to control. It automatically switches to a high suction rate when necessary, relieving the surgeon of the burden of himself or herself controlling this parameter of operation. Furthermore, controlling the input through the conduit 11 in accordance with actually detected pressure while merely switching the suction between two levels makes the equipment simple and foolproof.

We claim:

1. An apparatus for circulating a physiological liquid at a pressure and flow rate through a body cavity for an endoscopic resection or examination of the cavity, the apparatus comprising:
    a source of the liquid;
    an input pump connected to the source and having a feed conduit for extending into the cavity for supplying the liquid to the cavity;
    sensor means for detecting pressure in the cavity and for generating an output corresponding to the detected pressure;
    generator means for generating an output corresponding to a reference pressure;
    means including an input-pump comparator connected to the input pump and having inputs connected to the sensor means and to the generator means for receiving the outputs therefrom and for operating the input pump such that the detected pressure corresponds at least generally to the reference pressure;
    a suction pump having a main suction conduit extending into the cavity for aspirating the liquid therefrom; and
    suction control means for operating the suction pump at a predetermined generally uniform rate, said suction pump being a volumetric pump having a drive motor, the suction control means including
    a tachometer connected to the motor,
    means for generating a motor-speed set point, and a suction pump comparator having inputs connected to the set-point generating means and to the tachometer for comparing the actual motor speed detected with the motor-speed set point and having an output operatively connected to the motor for slowing the motor when the actual speed exceeds the set point and for speeding up the motor when the actual speed drops below the set point.

2. The apparatus defined in claim 1 wherein the set-point generating means can generate two different set points and selectively feeds same to the suction-pump comparator.

3. The apparatus defined in claim 1, further comprising:
    a suction-pump shutdown switch connected between the suction pump and the suction-pump comparator;
    means for generating a low-pressure limit output;
    shutdown comparator connected to the low-pressure output generator means and to the sensor means for opening the shutdown switch and stopping the suction pump when the pressure detected by the shutdown comparator is less than the low-pressure limit.

4. An apparatus for circulating a physiological liquid at a pressure and flow rate through a body cavity for an endoscopic resection or examination of the cavity, the apparatus comprising:
    a source of the liquid;
    an input pump connected to the source and having a feed conduit for extending into the cavity for supplying the liquid to the cavity;
    sensor means for detecting pressure in the cavity and for generating an output corresponding to the detected pressure;
    generator means for generating an output corresponding to a reference pressure;
    means including an input-pump comparator connected to the input pump and having inputs connected to the sensor means and to the generator means for receiving the outputs therefrom and for operating the input pump such that the detected pressure corresponds at least generally to the reference pressure;
    a suction pump having a main suction conduit extending into the cavity for aspirating the liquid therefrom;
    suction control means for operating the suction pump at a predetermined generally uniform rate;
    a tool insertable into the joint;
    an auxiliary suction conduit having an end opening at the tool and an opposite end; and
    valve means having an output connected to the suction pumps and two alternately selectable inputs, one connected to the main suction conduit and the other to the auxiliary suction conduit, the valve means being movable between a position connecting the suction pump to only the main suction conduit and a position connecting the suction pump to only the auxiliary suction conduit.

5. The apparatus defined in claim 4 wherein the tool has a blade and the apparatus further comprises a switch closable for rotating the blade.

6. In an endoscopic procedure wherein a liquid is fed into the joint from a feed pump through a feed conduit and is drawn out of the joint by a suction pump through a main suction conduit and wherein a tool carrying one end of an auxiliary suction conduit can also be inserted into the joint and the auxiliary suction conduit is connectable to the suction pump, the method comprising the steps of:

- operating the suction pump at a rate corresponding to a generally constant low rate of flow in the suction conduit when the suction pump is connected to the main suction conduit;
- increasing the suction-pump rate to a predetermined relatively high rate when the auxiliary conduit is connected to the suction pump;
- detecting the pressure in the joint; and
- operating the feed pump in accordance with the detected pressure in the joint to maintain the pressure above a predetermined desired level.

7. The method defined in claim 6, further comprising the step of stopping the pumps when the pressure detected in the joint drops below a predetermined minimum level.

8. The method defined in claim 7 wherein the tool includes a blade and a motor operable to move the blade, the method further comprising the step of:

- automatically disconnecting the suction pump from the main suction conduit and connecting the suction pump to the auxiliary suction conduit and simultaneously increasing the suction-pump rate from the low rate to the high rate when the motor is operated to move the blade.

9. An endoscopic examination/resection apparatus comprising:

- a source of a physiological liquid;
- means including a feed pump and a feed conduit insertable into a joint for feeding the liquid to the joint;
- means including a suction pump and a main suction conduit for drawing the liquid out of the joint;
- a tool insertable into the joint and carrying one end of an auxiliary suction conduit;
- valve means between the suction conduits and the suction pump for connecting the suction conduits alternately to the suction pump to withdraw liquid from the joint through the conduits;
- suction-pump control means for operating the suction pump at a rate corresponding to a generally constant low rate of flow in the suction conduit when the suction pump is connected by the valve means to the main suction conduit;
- speed control means for increasing the suction-pump rate to a predetermined relatively high rate when the auxiliary conduit is connected by the valve means to the suction pump; and
- feed-pump control means for detecting the pressure in the joint and for operating the feed pump in accordance with the detected pressure in the joint to maintain the detected pressure above a predetermined desired level.

10. The apparatus defined in claim 9, further comprising emergency cutout means connected to the control means and to the pumps for stopping the pumps when the pressure detected in the joint drops below a predetermined minimum level.

11. The apparatus defined in claim 9 wherein the tool is provided with a blade and a motor operable to move the blade, the apparatus further comprising means for automatically disconnecting the suction pump from the main suction conduit and connecting the suction pump to the auxiliary suction conduit when the motor is operated to move the blade.

* * * * *